(12) United States Patent
Fenton et al.

(10) Patent No.: US 10,367,178 B2
(45) Date of Patent: Jul. 30, 2019

(54) TAMPER PROOF BATTERY ENCLOSURE

(71) Applicant: Sky Medical Technology Ltd., Cheshire (GB)

(72) Inventors: Jonathan Fenton, Greenwich (GB); Ali Ersan, London (GB); Martin Gordon, Buckinghamshire (GB)

(73) Assignee: Sky Medical Technology Ltd., Cheshire (GB)

( * ) Notice: Subject to any disclaimer, the term of this patent is extended or adjusted under 35 U.S.C. 154(b) by 76 days.

(21) Appl. No.: 15/540,769

(22) PCT Filed: Jan. 7, 2016

(86) PCT No.: PCT/BG2016/050033
§ 371 (c)(1),
(2) Date: Jun. 29, 2017

(87) PCT Pub. No.: WO2016/110706
PCT Pub. Date: Jul. 14, 2016

(65) Prior Publication Data
US 2018/0026240 A1   Jan. 25, 2018

(30) Foreign Application Priority Data

Jan. 7, 2015   (GB) .................................. 1500164.7

(51) Int. Cl.
*A61N 1/04*   (2006.01)
*H01M 2/10*   (2006.01)
(Continued)

(52) U.S. Cl.
CPC ........ *H01M 2/1044* (2013.01); *A61N 1/0452* (2013.01); *A61N 1/0492* (2013.01);
(Continued)

(58) Field of Classification Search
CPC ........... H01M 2/1044; H01M 10/4257; H01M 2010/4271; H01M 2220/30; A61N 1/0452; A61N 1/36003; A61N 1/36014
See application file for complete search history.

(56) References Cited

U.S. PATENT DOCUMENTS

| | | | |
|---|---|---|---|
| 4,070,821 A | 1/1978 | Somogyi |
| 4,190,748 A | 2/1980 | Langford |

(Continued)

FOREIGN PATENT DOCUMENTS

| | | |
|---|---|---|
| DE | 37 16 379 A1 | 11/1987 |
| EP | 2 757 566 A1 | 7/2014 |

(Continued)

OTHER PUBLICATIONS

International Search Report and Written Opinion dated Mar. 23, 2016 in connection with International Application No. PCT/GB2016/050032.

(Continued)

*Primary Examiner* — Paula J Stice
(74) *Attorney, Agent, or Firm* — Wolf, Greenfield & Sacks, P.C.

(57) ABSTRACT

A neuromuscular stimulator device is described having a plastic casing housing control electronics which are maintained in contact with a power source by a metal retaining clip. The casing includes an integral cover which may be opened by breaking lines of weakness formed in the cover. The cover and clip are of such relative sizes and shapes so that once the cover is open, the clip may only be removed from the casing by deforming the clip. This deformation will ensure that the clip and other components cannot be replaced back in the casing, such that the device cannot easily be reused. In addition, the cover is not replaceable, due to the broken portions of the casing.

26 Claims, 4 Drawing Sheets

(51) Int. Cl.
*H01M 10/42* (2006.01)
*A61N 1/36* (2006.01)

(52) U.S. Cl.
CPC ..... *A61N 1/36003* (2013.01); *A61N 1/36014* (2013.01); *H01M 10/4257* (2013.01); *H01M 2010/4271* (2013.01); *H01M 2220/30* (2013.01)

(56) References Cited

U.S. PATENT DOCUMENTS

| | | |
|---|---|---|
| 4,322,587 A | 3/1982 | Burns et al. |
| 4,323,740 A | 4/1982 | Balash |
| 4,763,308 A | 8/1988 | Morata |
| 4,896,178 A | 1/1990 | Ohmura et al. |
| 5,752,087 A | 5/1998 | Sangregory |
| 6,355,316 B1 | 3/2002 | Miller et al. |
| 7,764,936 B2 | 7/2010 | Nakasono et al. |
| 2004/0026222 A1 | 2/2004 | Adachi |
| 2014/0014730 A1 | 1/2014 | Ledevehat |
| 2014/0097073 A1 | 4/2014 | Kikuchi |
| 2014/0316310 A1* | 10/2014 | Ackermann ....... A61N 1/36046 601/46 |
| 2018/0001076 A1 | 1/2018 | Fenton et al. |

FOREIGN PATENT DOCUMENTS

| | | |
|---|---|---|
| GB | 2210699 A | 6/1989 |
| GB | 2487758 A | 8/2012 |
| JP | 2002257960 A | 9/2002 |
| JP | 3875716 B1 | 1/2007 |
| WO | WO 99/03186 A | 1/1999 |
| WO | WO 2010/070332 A1 | 6/2010 |

OTHER PUBLICATIONS

International Preliminary Report on Patentability dated Jul. 20, 2017 in connection with International Application No. PCT/GB2016/050032.

International Search Report and Written Opinion dated Apr. 18, 2016 in connection with International Application No. PCT/GB2016/050033.

International Preliminary Report on Patentability dated Jul. 20, 2017 in connection with International Application No. PCT/GB2016/050033.

GB Search Report dated Jun. 25, 2015 in connection with GB Application No. GB1500164.7.

GB Search Report dated Jul. 2, 2015 in connection with GB Application No. GB1500163.9.

* cited by examiner

TAMPER PROOF BATTERY ENCLOSURE

RELATED APPLICATIONS

This application is a 371 U.S. National Stage of International Application No. PCT/GB2016/050033 filed on Jan. 7, 2016, which claims priority to United Kingdom Application No. 1500164.7 filed on Jan. 7, 2015.

FIELD OF THE INVENTION

The present invention relates to a tamper proof battery enclosure for incorporation into an electronic device. Aspects of the invention relate to an electronic device including such an enclosure. In particular, the enclosure is useful in disposable medical devices, for example an electronic neurostimulator device.

BACKGROUND TO THE INVENTION

Low cost, disposable electronic devices are used in many fields, including the medical device field. The present applicants have previously described an electronic neurostimulator device, in international patent application WO2010/070332. The device described therein incorporates a control unit housing the necessary electronics to drive the device, and to allow a user to operate the device; these typically include a PCB and an electrical cell. A pair of electrodes driven by the control unit are printed onto a flexible electrically insulative substrate The substrate is mounted onto a more robust elongate tongue made from, for example, a flexible plastics material.

It is desirable for disposable single use or short term use electronic devices to be, firstly, tamper proof, to prevent unauthorised access or modification to the electronics, and, secondly, readily disabled prior to disposal, again to prevent unauthorised reuse. Indeed, such requirements may be imposed as part of the regulatory procedure for medical devices.

It is among the objects of embodiments of the present invention to provide such properties to a device.

SUMMARY OF THE INVENTION

According to a first aspect of the present invention, there is provided an electronic device comprising:
  a plastic casing defining an interior and an exterior, the interior defining a cavity housing a printed circuit board, an electrical cell, and a metal retaining clip for retaining said electrical cell in electrical contact with the PCB, the casing comprising an integral cover which permits access to the interior of the casing;
  wherein the integral cover is formed as part of the casing, and includes portions of relative weakness joining the cover to the remainder of the casing, such that said weak portions may be broken by the application of sufficient force, to allow at least a part of the cover to be separated from the remainder of the casing, thereby creating an aperture permitting access to the interior of the casing;
  and wherein the retaining clip separates the electrical cell from the cover, and the clip and cover are of suitable relative size and shape so as to cause the clip to be deformed on application of sufficient force to remove the clip through the aperture created on separation of the cover.

Thus, the device is so arranged such that the aperture is smaller than the clip, and the clip will be deformed when removed from the casing; this deformation will ensure that the clip and other components cannot be replaced back in the casing, such that the device cannot easily be reused. In addition, the cover is not replaceable, due to the broken portions of the casing.

Preferably the cover comprises a flange at a first location, to allow a user to apply force at said location in order to break said portions of relative weakness. The flange may act as a fulcrum for a lever, allowing the cover to be removed using a suitable tool (for example, a screwdriver or similar).

Preferably the cover is joined to the remainder of the casing along a first side by said portions of relative weakness, and along a second side by a further weaker portion which said further portion forms a hinge when the weaker portions along the first side are broken. When the cover comprises a flange, the flange may be located along said first side of the cover. Preferably the hinge portion is arranged to break on application of additional force to the cover; this serves to further place the device beyond use.

Preferably the clip is sized to extend across said aperture and includes a first portion extending beyond said aperture within the interior of the casing such that said first clip portion cannot be removed from the interior through the aperture without deformation of the first clip portion. Thus, the clip is essentially too large to pass through the aperture unless it is deformed so that it cannot be used again.

Preferably the clip is non-resilient, such that upon deformation the clip does not revert to the original shape.

Preferably the electrical cell is sized to extend across said aperture and beyond said aperture on a first side. Preferably said first side of the cell is adjacent said hinge side of the cover. This arrangement allows the cell to act as a pivot whereby the hinge may be caused to break when the cell (and optionally the PCB) are removed from the casing. In certain embodiments, the PCB may be located adjacent the cover, such that breakage of the portions of relative weakness and separation of the at least part of the cover also serves to displace the PCB with respect to the cell and clip to thereby damage at least one of the PCB and/or clip.

The device preferably further comprises a flexible electrically insulative substrate on which is carried a pair of electrodes connected to the PCB by an electrically conductive pathway.

Preferably the casing is substantially sealed against moisture ingress. Preferably the casing is injection moulded.

The device is preferably a medical device, more preferably an electrical neuromuscular stimulator.

The device may further comprise a flexible electrically insulative substrate on which is carried an electrically conductive pathway, the pathway being in electrical contact with the PCB; wherein the substrate is located adjacent the cover, such that breakage of the portions of relative weakness also serves to damage the substrate, such that the electrically conductive pathway is interrupted. This feature may also form a separate embodiment.

In an alternative embodiment, there is provided an electronic device comprising:
  a plastic casing defining an interior and an exterior, the interior defining a cavity housing a printed circuit board, an electrical cell, and a metal retaining clip for retaining said electrical cell in electrical contact with the PCB, the casing comprising an integral cover which permits access to the interior of the casing; and a flexible electrically insulative substrate on which is carried an electrically conductive pathway, the pathway being in electrical contact with the PCB;

wherein the integral cover is formed as part of the casing, and includes portions of relative weakness joining the cover to the remainder of the casing, such that said weak portions may be broken by the application of sufficient force, to allow at least a part of the cover to be separated from the remainder of the casing, thereby creating an aperture permitting access to the interior of the casing;

wherein the substrate is located adjacent the cover, such that breakage of the portions of relative weakness also serves to damage the substrate, such that the electrically conductive pathway is interrupted.

DETAILED DESCRIPTION OF THE INVENTION

Figure 1:
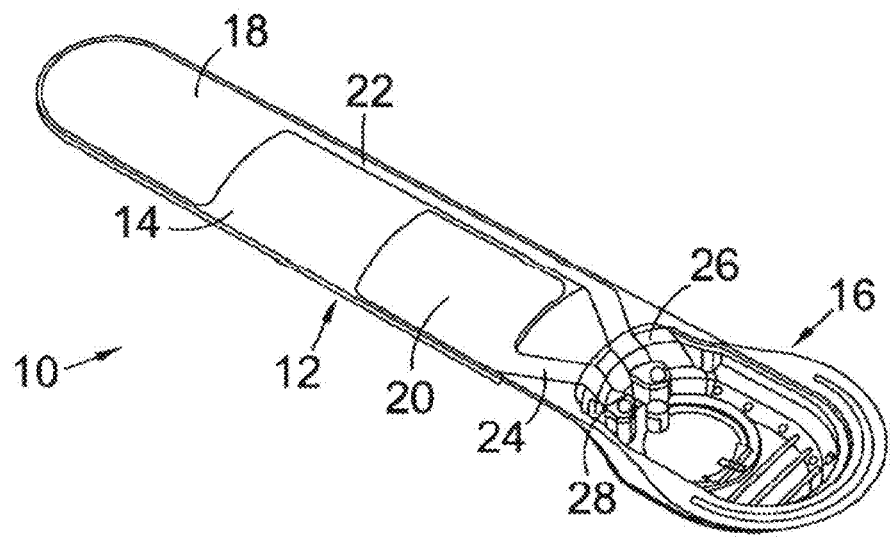
FIG. 1 shows an electronic neuromuscular stimulation device, taken from WO2010/070332.

Shown in FIG. 1 is a neuromuscular stimulator device 10 as described in WO2010/070332, The device comprises a flexible, non-stretchable thermoplastic elastomer substrate 12 which includes an elongate tongue 14 at one end, and a moulded recess 16 at the other.

On the tongue 14 are printed positive 18 and negative 20 electrodes. The positive is slightly larger than the negative. Each electrode includes a conductive track 22, 24 leading from the electrode to a respective contact point 26, 28 located in the recess 16.

Not shown in the figures are an insulative strip arranged between the positive track 22 and the negative electrode 20, and similar strips at the edges of the tongue, to prevent unwanted leakage of current.

Within the recess 16 are placed an electrical cell (not shown), and a PCB (not shown) including suitable circuitry to control the electrodes. Together with the conductive tracks 22, 24 and contact points 26, 28, this forms a complete circuit. A plastic cover is then sonically welded over the recess 16 to seal the components. A layer of gel is then placed over the whole device 10; this provides an electrical contact with a user's limb and helps keep the device adhered to a user. The gel may be protected in transit by a peelable backing layer.

Figure 2:
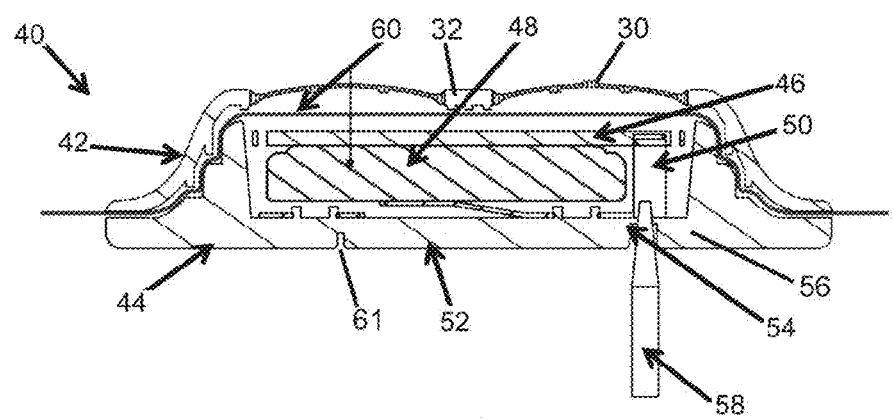
FIG. 2 shows a section of a casing for an electronic neuromuscular stimulation device, incorporating a tamper proof battery enclosure in accordance with a first embodiment of the present invention.

The outer surface of the recess 16 is formed with an integral diaphragm button 30 and an aperture 32 for displaying an LED (visible in FIG. 2). The button 30 is arranged to contact a corresponding button on the battery housing or PCB to activate the device. The aperture 32 displays an LED which indicates whether the device is operating.

Figure 7:
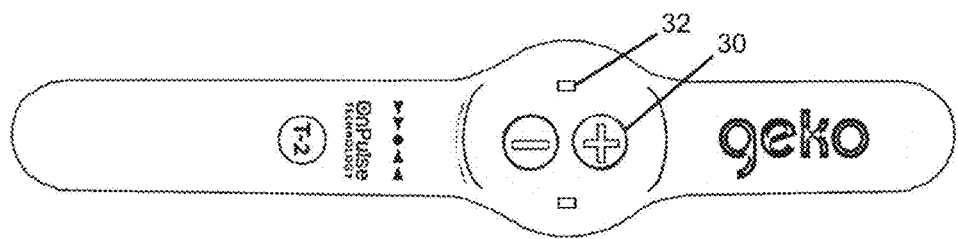
FIGS. 7 and 8 show external views of an alternative device.
Figure 8:
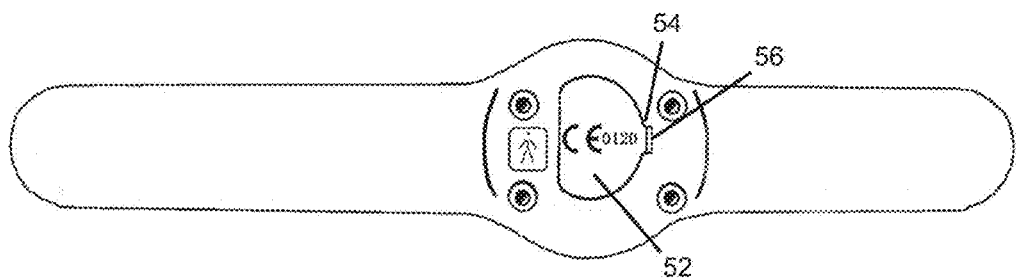

An alternative device is shown in external view in FIGS. 7 and 8. This is generally similar in operation to the device shown in FIG. 1, but has a slightly different configuration, in that the recess/enclosure is located towards the centre of the flexible tongue. A view of the device from the lower surface is shown in FIG. 8; in particular the cover of the casing can be seen here.

FIG. 2 shows a sectional view of a casing of the device of FIGS. 7 and 8 (corresponding generally to the recess 16 of the device shown in FIG. 1, and corresponding to the dotted line shown in FIG. 7) incorporating a tamper proof enclosure in accordance with a first embodiment of the present invention. The casing 40 includes upper 42 and lower 44 portions ultrasonically welded together to form a sealed unit. An enclosure is formed within the casing, within which are located a PCB 46, an electrical cell 48, and a metal clip 50. Extending above the PCB 46 is a flexible insulative substrate 60 which extends beyond the casing 40 via a path formed from the upper and lower casing portions. The substrate 60 carries electrically conducting paths in contact with the PCB, leading to electrodes outside the casing for placing in contact with a user to electrically stimulate their muscles.

Figure 4:
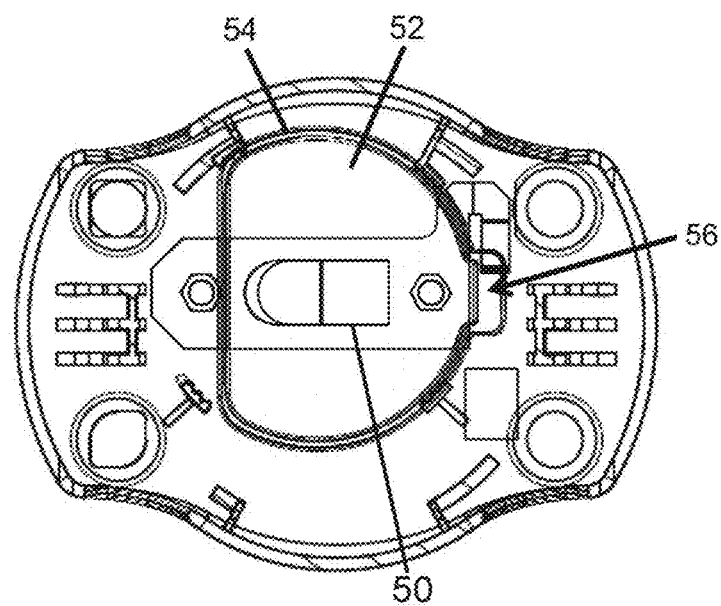
FIG. 4 shows a bottom view of the casing of FIG. 2.

On the lower portion 44 of the casing 40 is formed a cover 52, which is defined by a thinner portion 54 extending around the cover 52, joining it to the rest of the casing. As can be seen in FIG. 4 (a bottom view of the casing 40), the thinner portion 54 extends around the cover 52 and incorporates a flange 56 at one side. As also apparent from FIG. 4, the clip 50 is sized so as to extend across the whole width of the cover and beyond, into the enclosure formed by the casing. At the side of the cover forming a flange, the clip 50 also extends upwards along the side of the cell 48 (visible in FIG. 2).

The device incorporating the casing 40 is intended to be a disposable, single use (or few uses) device. After use, the cell 48 (and other electrical components) may be removed for recycling or disposal, and the device rendered inoperative.

Figure 3:
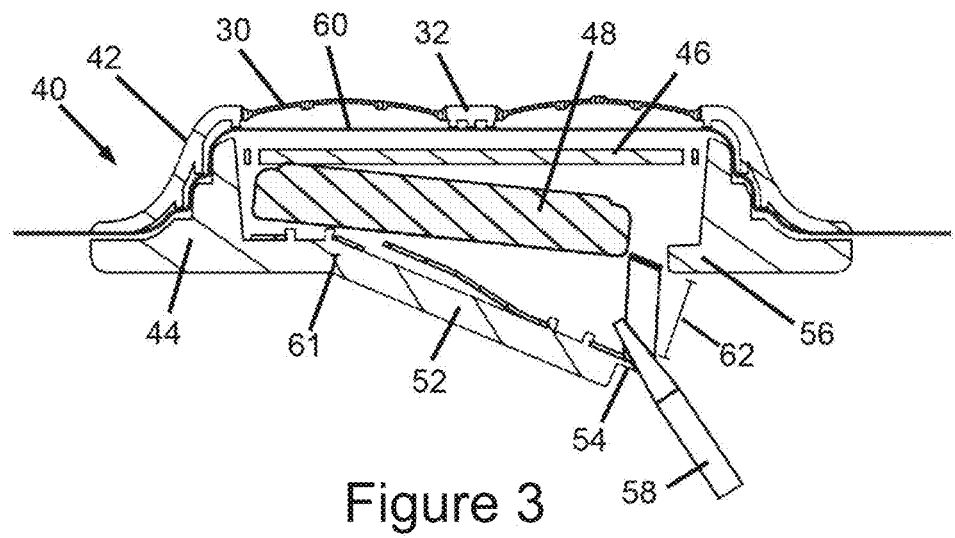
FIG. 3 shows the casing of FIG. 2, after it has been opened for disposal.

In order to remove the cell 48, a user may insert a tool 58 (for example, a screwdriver) under the flange 56 and lever the cover 52 open. The thinner portion 54 of the casing will break, and the opposite side from the flange acts as a hinge 61 (FIG. 3). The cell 48 and clip 50 may then be levered out of the casing 40. As the aperture 62 formed by the opening of the cover 52 is somewhat narrower than the cell 48 and the clip 50, the clip (and in particular the portion of the clip extending upwards alongside the cell 48) will be deformed upon removal, rendering it inoperative to electrically connect the cell to the PCB. Further, the cell 48 may also be arranged so as to act to completely separate the cover 52 from the remainder of the casing 40. Thus, the cell, clip, and PCB may be removed from the casing and recycled, while the casing and clip are damaged such that they cannot be reassembled and reused.

Figure 5:
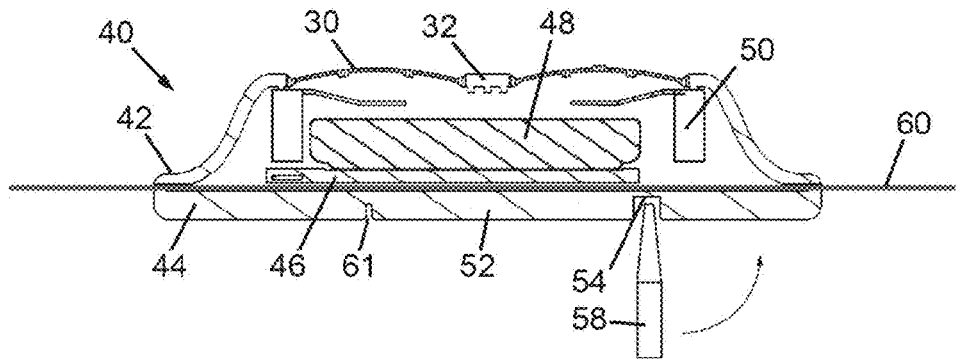
FIG. 5 shows a section of a casing incorporating a tamper proof battery enclosure in accordance with a second embodiment of the present invention.
Figure 6:
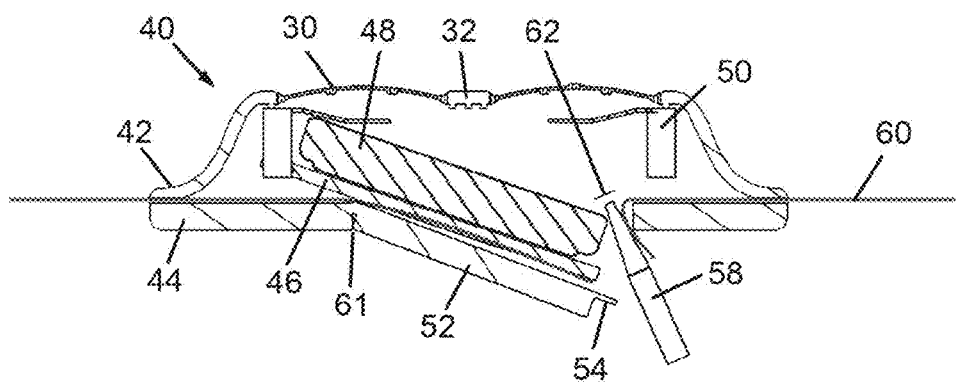
FIG. 6 shows the casing of FIG. 5, after it has been opened for disposal.

An alternative embodiment is shown in FIGS. 5 and 6. In this embodiment, the substrate 60 is arranged so as to be adjacent the cover 52, with the PCB 46 and cell 48 being arranged in electrical contact with the substrate 60. The clip 50 in this embodiment is somewhat different, in that it is not deformed on opening of the cover and removal. Instead, when a user opens the cover 52 to remove the cell and PCB, this causes the substrate 60 to be damaged or broken, thereby interrupting the electrical connection between the PCB and the electrodes, and rendering the device inoperable. In addition, in this embodiment the PCB is located adjacent the cover, such that breakage of the portions of relative weakness and separation of the at least part of the cover also serves to displace the PCB with respect to the cell and clip to thereby damage at least one of the PCB and/or clip.

This embodiment may be combined with the first embodiment, such that a tamper proof enclosure incorporates both means of rendering the device inoperative.

The invention claimed is:

1. An electronic device comprising:
   a plastic casing defining an interior and an exterior, the interior defining a cavity housing a printed circuit board, an electrical cell, and a metal retaining clip for retaining said electrical cell in electrical contact with the printed circuit board, the casing including an integral cover which is configured to permit access to the interior of the casing;
   wherein the integral cover is formed as part of the casing, and the cover is a portion of the casing, and the casing includes portions which are configured to be weaker relative to the cover, said portions joining the cover to a remainder of the casing, such that said portions may be broken by the application of sufficient force, to allow at least a part of the cover to be separated from the remainder of the casing, thereby creating an aperture permitting access to the interior of the casing;
   and wherein the retaining clip separates the electrical cell from the cover, and the retaining clip is larger than the aperture.

2. The device of claim 1, wherein the cover comprises a flange at a location to allow a user to apply force at said location in order to break said portions which are configured to be weaker relative to the cover.

3. The device of claim 2, wherein the cover is joined to the remainder of the casing along a first side of the cover by said portions which are configured to be weaker relative to the cover, and along a second side of the cover by an additional portion which is configured to be weaker relative to the cover, which said additional portion forms a hinge when the portions which are configured to be weaker relative to the cover along the first side of the cover are broken.

4. The device of claim 3, wherein said flange is located along said first side of the cover.

5. The device of claim 3, wherein the retaining clip is sized to extend across said aperture and includes a first portion extending beyond said aperture within the interior of the casing such that said first portion cannot be removed from the interior through the aperture without deformation of the first portion.

6. The device of claim 3, wherein said hinge is arranged to break on application of additional force to the cover.

7. The device of claim 3, wherein the electrical cell is sized to extend across said aperture and beyond said aperture on a first side of the electrical cell.

8. The device of claim 7, wherein said first side of the electrical cell is adjacent said second side of the cover.

9. The device of claim 1, wherein said retaining clip is non-resilient, such that upon deformation the retaining clip does not revert to an original shape of the retaining clip.

10. The device of claim 1, further comprising a flexible electrically insulative substrate on which is carried a pair of electrodes connected to the printed circuit board by an electrically conductive pathway.

11. The device of claim 1, wherein the casing is sealed against moisture ingress.

12. The device of claim 1, wherein the casing is injection moulded.

13. The device of claim 1, wherein the device is a medical device.

14. The device of claim 13, wherein the medical device is an electrical neuromuscular stimulator.

15. The device of claim 1, further comprising a flexible electrically insulative substrate on which is carried an electrically conductive pathway, the pathway being in electrical contact with the printed circuit board;
   wherein the substrate is located adjacent the cover, such that breakage of the portions which are configured to be weaker relative to the cover also serves to damage the substrate, such that the electrically conductive pathway is interrupted.

16. An electronic device comprising:
   a plastic casing defining an interior and an exterior, the interior defining a cavity housing a printed circuit board, an electrical cell, and a metal retaining clip for retaining said electrical cell in electrical contact with the printed circuit board, the casing including an integral cover configured to permit access to the interior of the casing; and
   a flexible electrically insulative substrate on which is carried an electrically conductive pathway, the pathway being in electrical contact with the printed circuit board;
   wherein the integral cover is formed as part of the casing, and the cover is a portion of the casing, and the casing includes portions which are configured to be weaker relative to the cover, said portions joining the cover to a remainder of the casing, such that said portions may be broken by the application of sufficient force, to allow at least a part of the cover to be separated from the remainder of the casing, thereby creating an aperture permitting access to the interior of the casing;
   wherein the substrate is located adjacent the cover such that breakage of the portions which are configured to be weaker relative to the cover also serves to damage the substrate, such that the electrically conductive pathway is interrupted.

17. The device of claim 16, wherein the cover comprises a flange at a location to allow a user to apply force at said location in order to break said portions which are configured to be weaker relative to the cover.

18. The device of claim 17, wherein the cover is joined to the remainder of the casing along a first side of the cover by said portions which are configured to be weaker relative to the cover, and along a second side of the cover by an additional portion which is configured to be weaker relative to the cover, which said additional portion forms a hinge when the portions which are configured to be weaker relative to the cover along the first side of the cover are broken.

19. The device of claim 18, wherein said flange is located along said first side of the cover.

20. The device of claim 18, wherein said hinge is arranged to break on application of additional force to the cover.

21. The device of claim 16, wherein the electrical cell is sized to extend across said aperture and beyond said aperture on a first side of the electrical cell.

22. The device of claim 16 wherein the flexible electrically insulative substrate further carries a pair of electrodes connected to the electrically conductive pathway.

23. The device of claim 16, wherein the casing is sealed against moisture ingress.

24. The device of claim 16, wherein the casing is injection moulded.

25. The device of claim 16, wherein the device is a medical device.

26. The device of claim 25, wherein the medical device is an electrical neuromuscular stimulator.

* * * * *

UNITED STATES PATENT AND TRADEMARK OFFICE
CERTIFICATE OF CORRECTION

PATENT NO. : 10,367,178 B2  
APPLICATION NO. : 15/540769  
DATED : July 30, 2019  
INVENTOR(S) : Jonathan Fenton et al.

Page 1 of 1

It is certified that error appears in the above-identified patent and that said Letters Patent is hereby corrected as shown below:

On the Title Page

In the Section "PCT No." please replace "PCT/BG2016/050033" with --PCT/GB2016/050033--

Signed and Sealed this  
Nineteenth Day of May, 2020

Andrei Iancu  
*Director of the United States Patent and Trademark Office*